United States Patent [19]

Yoder et al.

[11] Patent Number: 5,871,462
[45] Date of Patent: Feb. 16, 1999

[54] METHOD FOR USING A FLUID JET CUTTING SYSTEM

[75] Inventors: Marvel John Yoder, Andover, Mass.; Frank Van Patterson, Exeter, N.H.; Timothy E. Moutafis, Gloucester, Mass.

[73] Assignee: Hydrocision, Inc., Wilmington, Mass.

[21] Appl. No.: 484,008

[22] Filed: Jun. 7, 1995

[51] Int. Cl.⁶ .................................................. B61B 17/20
[52] U.S. Cl. .............................. 604/22; 606/167; 604/49; 83/13
[58] Field of Search ................................. 604/19, 22, 49; 606/167; 83/13

[56] References Cited

U.S. PATENT DOCUMENTS

| | | |
|---|---|---|
| 3,818,913 | 6/1974 | Wallach . |
| 3,930,505 | 1/1976 | Wallach . |
| 4,111,490 | 9/1978 | Liesveld . |
| 4,465,438 | 8/1984 | Bräuer et al. . |
| 4,479,760 | 10/1984 | Bilstad . |
| 4,479,761 | 10/1984 | Bilstad . |
| 4,479,762 | 10/1984 | Bilstad . |
| 4,560,373 | 12/1985 | Sugino . |
| 4,662,829 | 5/1987 | Nehring . |
| 4,690,672 | 9/1987 | Veltrup . |
| 4,741,678 | 5/1988 | Nehring . |
| 4,761,039 | 8/1988 | Hilaris . |
| 4,776,769 | 10/1988 | Hilaris . |
| 4,795,217 | 1/1989 | Hilaris . |
| 4,798,339 | 1/1989 | Sugino et al. . |
| 4,811,902 | 3/1989 | Nagata . |
| 4,827,679 | 5/1989 | Earle, III . |
| 4,898,574 | 2/1990 | Uchiyama et al. . |
| 4,913,698 | 4/1990 | Ito et al. . |
| 4,937,985 | 7/1990 | Boers . |
| 4,950,238 | 8/1990 | Sullivan . |
| 5,018,670 | 5/1991 | Chalmers . |
| 5,037,431 | 8/1991 | Summers et al. . |
| 5,052,624 | 10/1991 | Boers . |
| 5,074,862 | 12/1991 | Rausis . |
| 5,092,744 | 3/1992 | Boers . |
| 5,125,582 | 6/1992 | Suriaatmadia et al. . |
| 5,133,687 | 7/1992 | Malloy . |
| 5,135,482 | 8/1992 | Neracher . |
| 5,162,016 | 11/1992 | Malloy . |
| 5,186,615 | 2/1993 | Karliner . |
| 5,201,643 | 4/1993 | Hirosawa et al. . |
| 5,205,779 | 4/1993 | O'Brien et al. . |
| 5,230,443 | 7/1993 | Du . |
| 5,309,899 | 5/1994 | Ginsberg . |
| 5,314,375 | 5/1994 | O'Brien et al. . |
| 5,322,504 | 6/1994 | Doherty et al. . |
| 5,364,234 | 11/1994 | Eickmann . |
| 5,368,452 | 11/1994 | Johnson . |
| 5,370,609 | 12/1994 | Drasler et al. . |

FOREIGN PATENT DOCUMENTS

| | | |
|---|---|---|
| 0280972 | 9/1988 | European Pat. Off. ................. 606/50 |
| 0 485133 A1 | 5/1992 | European Pat. Off. . |
| 0 489496 A1 | 6/1992 | European Pat. Off. . |
| WO 94/14584 | 12/1993 | WIPO . |

OTHER PUBLICATIONS

"A Critical Examination of the Use of Water Jets for Medical applications" 5th American Water Jet Conference Aug. 29–31, 1989 Toronto, Canada pp. 425–448.

Baer H.U., Maddern G.J. Blumgart L.H.: A new water jet dissector—initial experience in hepatic surgery, Br.J.Surg. 1991; 78:502–503.

Baer H.U., Maddern G.J., Blumgart L.H.; Hepatic surgery faciliated by a new jet dissector, HPB Surgery 1991; 4:137–146.

(List continued on next page.)

Primary Examiner—Mark Bockelman
Attorney, Agent, or Firm—Wolf, Greenfield & Sacks, P.C.

[57] ABSTRACT

A method of pin-pointing a fluid jet onto a target involves pumping fluid at a low pressure through a jet creating instrument, directing the low pressure jet onto a target and pumping the fluid at a higher pressure while maintaining the jet on the target.

8 Claims, 4 Drawing Sheets

OTHER PUBLICATIONS

Baer H.U., Maddern G.J., Dennison A.R., Blumgart L.H.; Water–jet dissection in hepatic surgery, Invasive Therapy 1992; 1:169–172.

Baer H.U., Dennison A.R., Maddern G.J., Blumgart L.H.; Subtotal hepatectomy: a new procedure based on the inferior hepatic vein. Br. J. Surg. 1991; 78:1221–1222.

Baer H.U., Blumgart L.H.: Anmerkungen zur Veroffentlichung von H.G. Rau et al.; Schneiden mit dem Wasserstrahl (Jetting Cutting)—eine Alternative zum Ultraschallaspirator? [Chirurg 1990; 61:7351] Chirurg 1991;62:356.

Terzis, A.J.A. et al., A New System for Cutting Brain Tissue Preserving Vessels: water jet cutting., Br. J. Neur. 1989, 3:361–66.

Giraud J–Y, et al., Bone Cutting, Clin. Phys. Phys. Meas. 1991, 12:1–19.

Field, J.E., The physics of liquid impact, shock wave interactions with cavities, and the implications to shock wave lithotripsy, Phys. Med. Biol. 1991, 11:1475–84.

Zhong P. et al., Propagation of shock waves in elastic solids caused by cavitation microjet impact, II: Application in extracorporeal shock wave lighotripsy, J. Acoust. Soc. Am. 1993, 94:29–36.

Izumi R, et al., Hepatic Resection Using a Water Jet Dissector, Jpn. J. Surg. 1993, 23:31–35.

Hepatotom Supersonic Microjet Dissector Product Literature Medical Exports (Date)?.

METHOD FOR USING A FLUID JET CUTTING SYSTEM

FIELD OF INVENTION

This invention relates a fluid jet cutting system, to components of such a system and to a method of pinpointing a fluid jet without damaging surrounding areas.

BACKGROUND OF THE INVENTION

Fluid jet cutting systems are known which employ high pressure streams of liquid, such as water, as the cutting force. High pressure fluid jet cutting systems also have been proposed for use in surgical applications. U.S. Pat. No. 3,930,505 discloses a variable pressure jet for disintegrating eye lens tissue. A system for use in hepatobiliary surgery, known as the Hepatom, has been reported in the literature and may be available outside of the United States. U.S. Pat. No. 5,370,609, and related European patent applications 0 485 133 and 0 489 496, describe a water jet catheter which delivers a high pressure liquid stream to dislodge, emulsify and remove deposits from a vein or artery.

SUMMARY OF THE INVENTION

The present invention is a system for generating a high pressure fluid jet including a variable pressure pump for creating the high pressure fluid and a burst resistant delivery tube for safely conducting the pressurized stream. The pump may include a disposable diaphragm pump which is driven by a reusable pump, such as a piston pump or an air intensifier unit. The pumped fluid communicates only with the disposable diaphragm component, allowing contamination free reuse of the system by simply replacing a spent diaphragm unit with a fresh, sterile disposable pump. An instrument or wand having one or more orifices for creating a jet may be connected to the distal end of the delivery tube. Alternatively, the jet instrument may embody a burst resistant catheter having a jet tip. The delivery tube may be coiled, enhancing the flexibility of the tube and the ease of handling by a user. A high pressure seal may be formed between the delivery tube and the outlet of the pump and between the nozzle and the delivery tube. The seal may be provided in a hand-tightenable connector where one or both of the foregoing junctions are detachable rather than permanent.

The present invention also is directed to a disposable component of the fluid jet system including a disposable diaphragm pump that has an inlet port connectable to a source of fluid to be pumped and an outlet port in communication with a pressure resistant delivery tube. The delivery tube is connectable, at a distal end, to an instrument having one or more fine orifices for creating the hair-thin fluid jet. The disposable diaphragm pump is mountable to a reusable pumping chamber which will generate the working force required to flex the diaphragm to fill and eject fluid from a pumping chamber.

The present invention also involves a fluid jet system including a high pressure pump having an inlet communicable with a source of jetting fluid and a coiled burst resistant delivery tube for conducting the pressurized stream. A jet nozzle may be integrally or detachably connected, in leaktight fashion, with a distal end of the delivery tube.

The present invention also involves a method of targeting a fluid jet. A fluid jet system is provided including a variable pressure pump, a source of fluid in communication with the pump, a delivery tube in communication with an outlet of the pump and an instrument in communication with the delivery tube having an orifice for creating a fluid jet as the pumped fluid exits therefrom. A visually observable "targeting" jet is created and directed towards the target at a low pressure which does not damage the target. The instrument is manipulated until the low pressure fluid beam is pinpointed onto the desired site. While maintaining the jet on the target, the pressure of the fluid is increased. The present method reduces the likelihood that areas surrounding the target site will be damaged while aiming of the high pressure jet.

It is an object of the present invention to provide a system for creating a high pressure fluid jet which is reusable without risk of contamination.

It is an additional object of the present invention to provide a system for creating a high pressure fluid jet which provides ease of handling for a user.

It is a further object of the present invention to provide a system for creating a high pressure fluid jet that can be precisely targeted at a low pressure that will not cause damage if misdirected or off the mark.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENT

Figure 1:
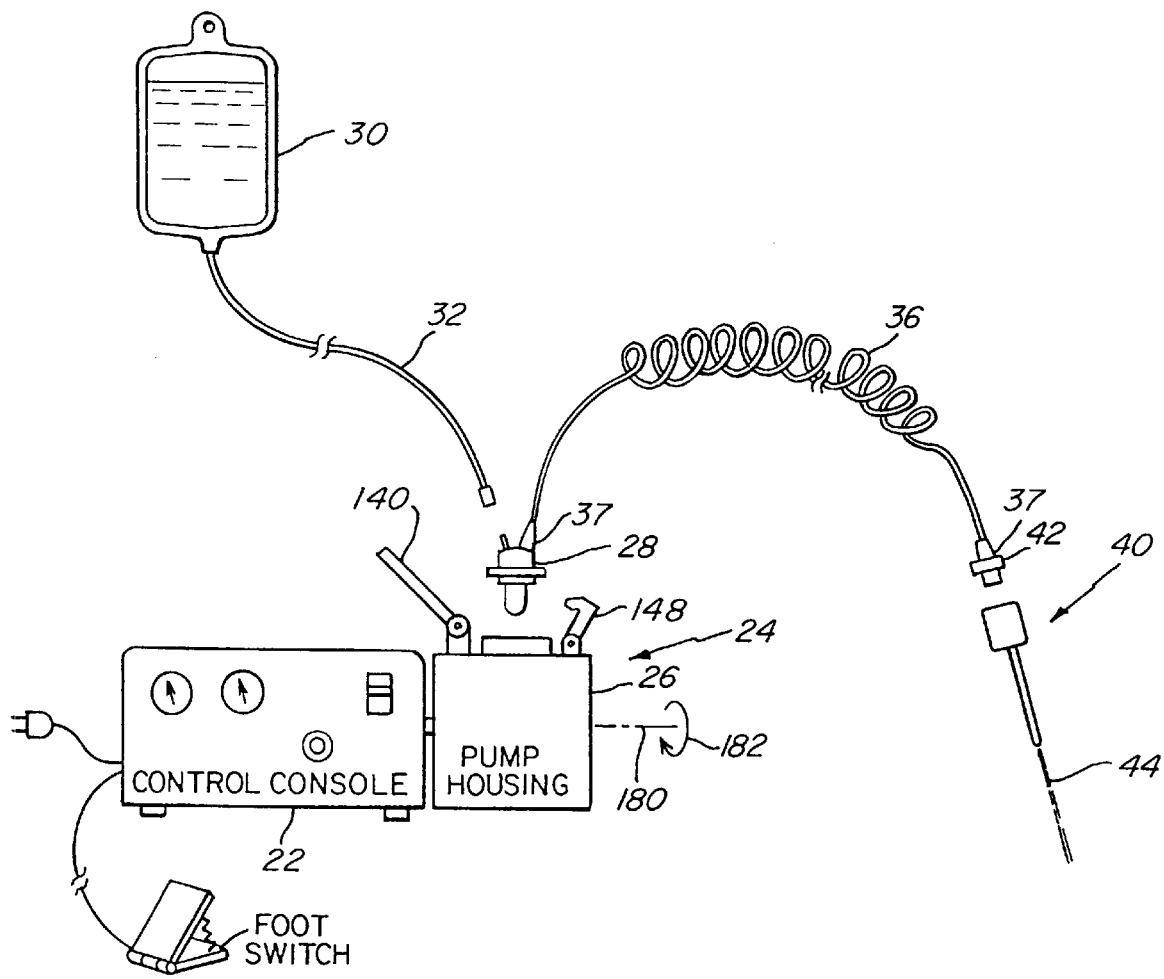
FIG. 1 is a schematic of a fluid jet cutting system according to the present invention specifically configured for use in surgical applications.

The present invention is a system for delivering a high pressure stream of cutting medium, preferably a liquid, against a target. Unlike a laser beam or a mechanical cutting instrument, the fluid jet does not generate localized heat which can thermally degrade regions surrounding the cutting site. The system allows controlled, accurate and fast cutting. The diameter of the jet stream and the pressure of the cutting medium may be selectively varied depending upon the application. The components of the cutting system may be integrally connected or, instead, detachable allowing the interchange of, for example, cutting tools, pump cartridges, etc. as required by the particular application or where wear or failure requires replacement. A pressure resistant delivery tube conducts the cutting fluid from the pump through an orifice which creates the fluid jet. The delivery tube may be coiled to enhance the maneuverability of the cutting stream. The fluid jet may be a coherent beam or may assume other configurations, such as an outwardly spreading spray, or a plurality of jet streams converging on a focal point, depending upon the number, orientation and shape of jet opening(s). The jet port may be provided in a hand-held instrument, allowing a user to manually position the fluid jet relative to the cutting site. The pump system may be reusable or, preferably, includes a reusable component and a limited use or disposable component which allows the portion of the pump which directly contacts the cutting fluid to be separately disposed of. The latter arrangement is particularly suitable where a sanitary or sterile cutting fluid or cutting site is desirable. The pressure and velocity of the fluid arc is selectively controllable allowing the user to pin-point a visually observable low pressure beam, having no significant cutting affect (from 10 to 1,000 p.s.i., and, preferably, about 200 p.s.i., depending on the material which is subject to cutting) on the cutting site before increasing the pressure of the fluid to within the cutting range (from 1,000 to 50,000 p.s.i. and, preferably, from 5,000 to 30,000 p.s.i., again depending on the material being cut). A dye may be provided in the fluid being jetted to enhance visualization. Targeting the jet in this manner permits precise and controlled cutting while reducing the incidence of unintentional damage of material surrounding the cutting site.

The fluid jet cutting system is contemplated for use in a wide variety of industrial applications including soft as well as hard materials. Articles such as fabric, food, foam and plastics, and specifically brittle or gummy materials which may stick to, or be fractured or deformed by, mechanical cutting blades appear well suited for fluid jet cutting. Sheets of baked goods, such as sticky fig or granola bars, may be cut into individual portions prior to packaging using the fluid jet system. Intricate shapes may be formed using the cutting beam, particularly when the movement of the jet is under computer control. Soft materials, such as foam or plastics may be cut without distortion of the final product. The fluid jet may be employed to core or drill materials and, for purposes of this application, the term "fluid jet cutting" is intended to be broadly construed and includes, without limitation, use of a high pressure fluid beam to cut, drill, core, perforate, strip, shape, delaminate and other forming and machining operations. The jet nozzle may be configured for holding in the hand of a user or for manipulation by machine control, such as an X,Y,Z coordinate machine positioner. The latter embodiment further suggests application of the jet cutting system on a commercial scale.

The fluid jet cutting system is particularly indicated for use in surgical procedures including, without limitation, orthopedic arthroscopic procedures. Selective variation of the jet stream pressure allows the surgeon to cut hard bone, soft bone, cartilage and tissue, to strip away tissue exposing underlying organs or vessels or, simply, to wash away blood and debris created by the surgical procedure. The latter irrigating function ensures good visibility of the operative site. Preferably, the jet is a fine, coherent steam of sterile cutting solution, such as physiological saline or, perhaps, a liquefied gas such as carbon dioxide, which cuts or ablates the tissue or bone, and the stream may then be used to pulverize the biological fragments into smaller pieces. The emulsified debris may be flushed or evacuated from the surgical site or the fragments can be removed using other techniques. When used in medical procedures, the pressurized fluid may contain vasoconstricting compounds to reduce bleeding, or anesthetic compounds to reduce pain or other useful compounds may be used to augment or facilitate a water jet medical procedure. The jet wand may include a suction nozzle or a separate suction line may be employed. Alternatively, positive pressure evacuation may be employed to remove the effluent.

Selective variation of the jet pressure allows the surgeon to target precisely a visible low pressure stream on the portion of the bone or tissue to be excised and then to cut the bone or tissue with the already pin-pointed jet simply by increasing the jet to a higher, cutting pressure. A physiologically inert dye may be dispersed in the sterile cutting fluid to enhance visualization of the low pressure stream. Even when fully submersed in fluid, the jet is ascertainable by the cavitation within the surrounding solution. The hair-thin fluid beam, having a diameter in the range of tenths of millimeters, preferably about 0.1 mm, permits the surgeon to make fine controlled incisions without damaging neighboring tissue, organs, vessels or nerves. A slender hand-holdable wand or nozzle may be employed, facilitating use of the fluid jet cutting system in surgical procedures which present narrow spaces and complicated geometries.

A fluid jet cutting system for use where sterility of the fluid jet is essential, such as in surgical applications, is illustrated in FIG. 1. A pump console 22 contains control circuitry and user information. Dials or buttons on the console allow the user to vary the parameters of the system. The console includes a reusable pump 26, in this case a piston pump, which is releasably engageable, in leaktight fashion, with a disposable diaphragm pump 28. A source of sterile cutting fluid, such as a saline bag 30 suspended from an IV pole, is placed in communication with the disposable pump via a flexible tube 32, shown disconnected in FIG. 1. The saline is forced under high pressure by the pump along a delivery tube 36 to a hand-held surgical jet wand 40. Flow of the cutting fluid is controlled by the surgeon through a foot switch which communicates with the pump control circuitry. The fluid delivery line 36 is formed of coiled stainless steel hypo tubing which has sufficient burst strength to safely conduct the high pressure fluid yet provides good maneuverability for the surgeon due to the coiled configuration. The hypotube preferably is formed of 14XH gauge (XH indicates extra heavy wall) type 316 or 304 stainless steel. The inner diameter of the tube shown is 0.036 inches and the outer diameter is 0.058 inches.

The hypotube may be formed by winding a straight length of tube on a mandrel, preferably 0.63 inches in diameter, such that adjacent coils are in contact. The ends of the hypotube remain uncoiled, providing a straight length upon which to mount hand-tightenable connectors or to integrally connect to the pump outlet and the jet nozzle instrument where the components are not desired to be detachable. Strain reliefs 37 may be mounted at the ends of the hypotube to prevent the hypotube from kinking adjacent to the connections to the pump outlet and jet nozzle instruments. The delivery tube may be provided in its compacted configuration, permitting the user to axially stretch the tube to the desired length and flexibility. In a representative embodiment, ten (10) feet of straight hypotube will yield approximately 4–6 feet of coiled delivery tube. The as-used coils have an inner diameter of 0.85 inches and approximately 2.5 windings per inch. The delivery tube preferably is rated for pressures in excess of 50,000 p.s.i.

A surgical jet instrument 40, preferably a wand that can be held in the hand of a surgeon, includes a lumen in communication with the delivery tube, that terminates in one or more fine axial or transverse jet orifice(s) having a diameter in the tenths of millimeters. Various configurations of the tip of the surgical jet wand may be employed. Preferably, the tip is selectively moldable allowing a surgeon to reshape or bend the jet tip into a configuration, or at an angle, which facilitates positioning of the nozzle relative to the surgical site. This feature is especially attractive where the operative field is difficult to reach.

A deflector or catcher may be provided opposite the orifice to transform the liquid jet into a harmless spray, preventing the fluid arc from cutting deeper than is desired or from attacking healthy tissue if the stream becomes misdirected. To ensure a small instrument profile, the catcher may be slidable (in the axial mode) or pivotable (in the transverse mode) from a slender configuration employed during insertion of the instrument to an expanded configuration at the surgical site. The slender configuration facilitates use of the instrument in arthroscopy and other procedures where small openings and narrow cannulas may be used to enter the operative field. Alternatively, one or more jets may be oriented to create a deflecting spray that accomplishes the same aim as the catcher. A separate outlet may be provided on the jet nozzle which is communicable at a proximal end (outside of the patient) with a source of suction, such as the main hospital supply, to allow aspiration of blood, surgical debris and the cutting fluid. Alternatively, a separate suction line may be employed. The separate outlet could also be an inlet for irrigation fluid or the infusion of medicaments. Alternatively, the surgical nozzle may be configured as the tip of a burst resistant catheter such as is disclosed in U.S. Pat. No. 5,370,609, the contents of which are incorporated herein by reference.

A quick connect adapter 42 may be provided at the end of the fluid line, allowing the surgeon to switch quickly amongst varying pre-shaped jet tips. In one embodiment of a hand tightenable connector between the coiled delivery tube and the jet wand, the coiled delivery tube includes a straight segment on one or both ends which is permanently fitted with a ferrule. An O-ring is slidably mounted over the tube end until it abuts the ferrule. The protruding tip of the delivery tube is received by an inlet of the jet wand or the outlet port of the pump. A thumb screw or other fastening mechanism draws the ferrule and O-ring into seating engagement in a stepped chamber having a reduced dimensioned recess for the O-ring (slightly smaller than the O-ring) and a larger chamber for the ferrule. The thumbscrew and ferrule may be configured to provide compatible surfaces, facilitating insertion of the ferrule into the stepped chamber as the thumbscrew and jet wand or outlet port are threadably engaged. The ferrule bottoms out against the floor of the chamber, deforming the O-ring a predetermined amount, but no more, so that a high pressure seal is affected between the first and second element without severely distorting the gasket so that the O-ring can be easily removed when the first and second bodies are separated.

The console includes a reusable working pump which is segregated from the sterile saline and a disposable pumping portion which acts directly on the saline, driving the sterile fluid at high pressure through the flexible delivery line 36, out of the surgical nozzle and into the operative site.

The two component pumping system works as follows. A non-sterile working fluid is forced by a piston head, in the reusable pump, against a flexible diaphragm in the disposable pump. Flexure of the diaphragm in response to the pressure of the working fluid reduces the volume in the disposable pumping chamber, forcing the physiologic solution through an outflow port, the coiled fluid line and, ultimately, the surgical jet wand. The diaphragm seats against the mouth of the working cylinder as the piston is retracted, drawing saline through an inflow port to refill the disposable pump chamber. The pumping system cycles repeatedly between filling and ejecting strokes, providing a nearly continuous, pulsating, flow of high pressure fluid to the jet wand. Check valves are provided in the inlet and outlet ports to ensure the desired flow paths. Upon completion of the procedure, the disposable diaphragm pump head is detached from the reusable piston pump and discarded or resterilized for reuse. The piston pump, which does not contact the sterile saline, may be reused with a new, sterile disposable diaphragm pump.

A second flexible diaphragm (not shown) may be mounted on the reusable pump at the cartridge interface. The second diaphragm operates to prevent undesirable material from entering the pump cylinder.

Figure 2:
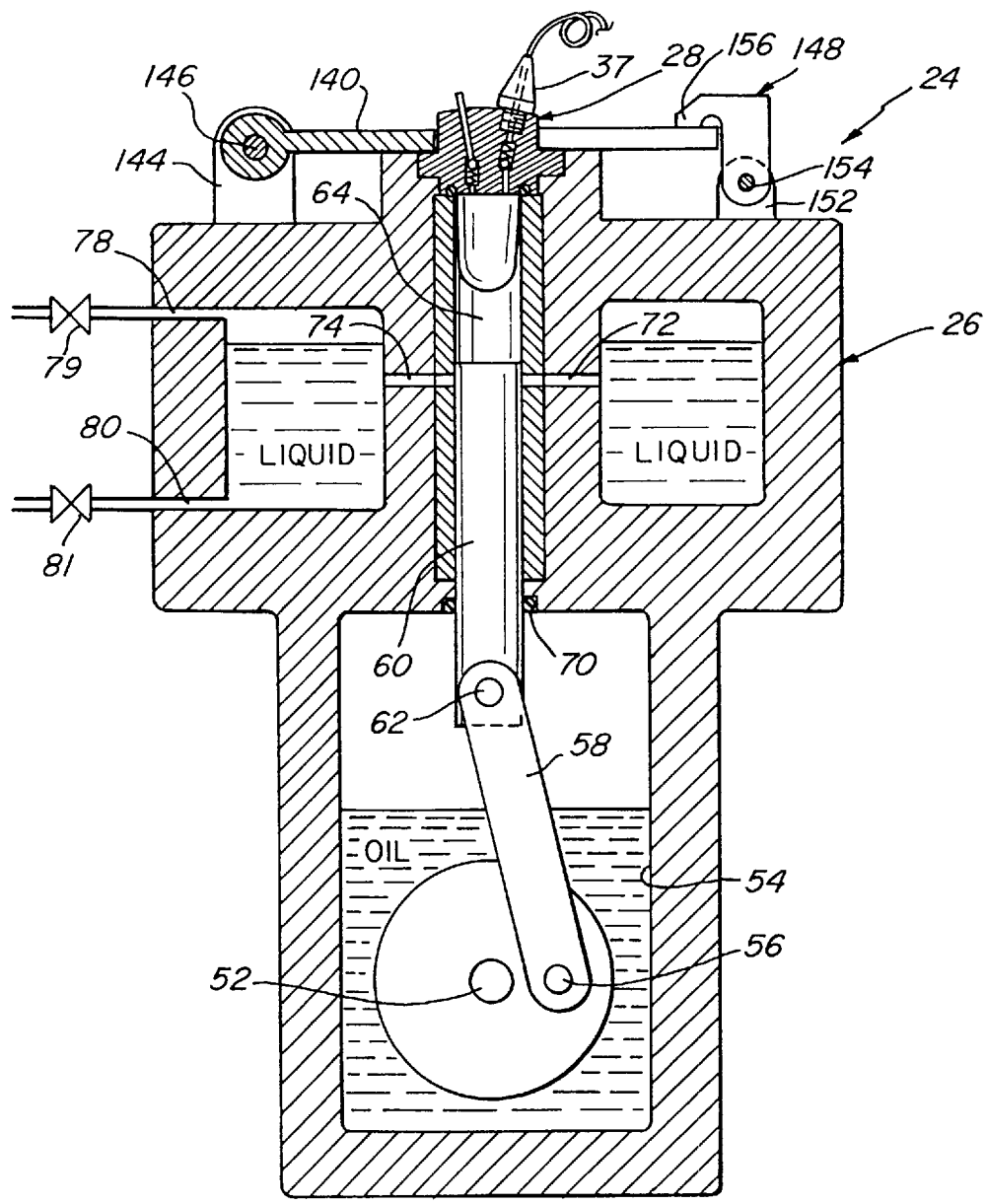
FIG. 2 is an illustration of the variable high pressure pump illustrated in FIG. 1.

FIG. 2 provides a detail view of an assembled pump, indicated generally by 24, including the reusable pump housing 26 and the disposable pump cartridge 28. Although a positive displacement piston pump is illustrated as the reusable component, other pumping mechanisms, such as an air intensifier, are contemplated as would be apparent to the ordinary practitioner. The reusable pump may be a pump disposed remote from the disposable diaphragm pump and connected to the diaphragm pump by a high pressure conduit. The reusable housing is preferably constructed of type 304 or 316 stainless steel. A shaft 52, driven by a motor (not shown), extends into a crank chamber 54. An eccentric crank 56 is mounted on the shaft and is engaged to an elongate linkage rod 58. Pin 62 connects the other end of the rod 58 to a cylindrical piston rod 60. The piston 60 preferably is made of carbide, however, other wear-resistant materials are suitable as would be apparent to those skilled in the art. Bearings (not shown) may be provided at each linkage connection to minimize friction between the respective moving parts. The chamber 54 is filled with a lubricating oil which also operates to reduce friction.

A cylindrical chamber 64, including a carbide containing insert, receives the piston. In a preferred form of the invention, the clearance between the cylindrical chamber 64 and the piston is 0.0002 inches. In a preferred embodiment, the diameter of the piston is approximately 0.25 inches.

Rotation of the shaft 52 causes the eccentric crank to move the linkage, reciprocating the piston within the chamber. The space in the chamber unoccupied by the piston forms the working fluid chamber. The piston reciprocates between a retracted position defining the largest volume of the chamber and an extended position where the unoccupied volume of the chamber is the smallest. The distance between the extended position and the retracted position is the piston stroke. In a preferred embodiment, the piston stroke is about 0.25 inches.

An annular seal 70 isolates the working chamber from the crank case. The seal is not subjected to the pressures of the working fluid chamber. Consequently, a conventional oil seal may be employed.

A pair of passages 72, 74 feed working fluid from a reservoir into the piston chamber. The passages open just slightly above the head of a fully retracted piston. Passages 78, 80 fluidly connect the annular chamber to the exterior of the pump, allowing water and air to flow between the annular chamber and the exterior of the housing through valves 79 and 81, respectively.

Figure 4:
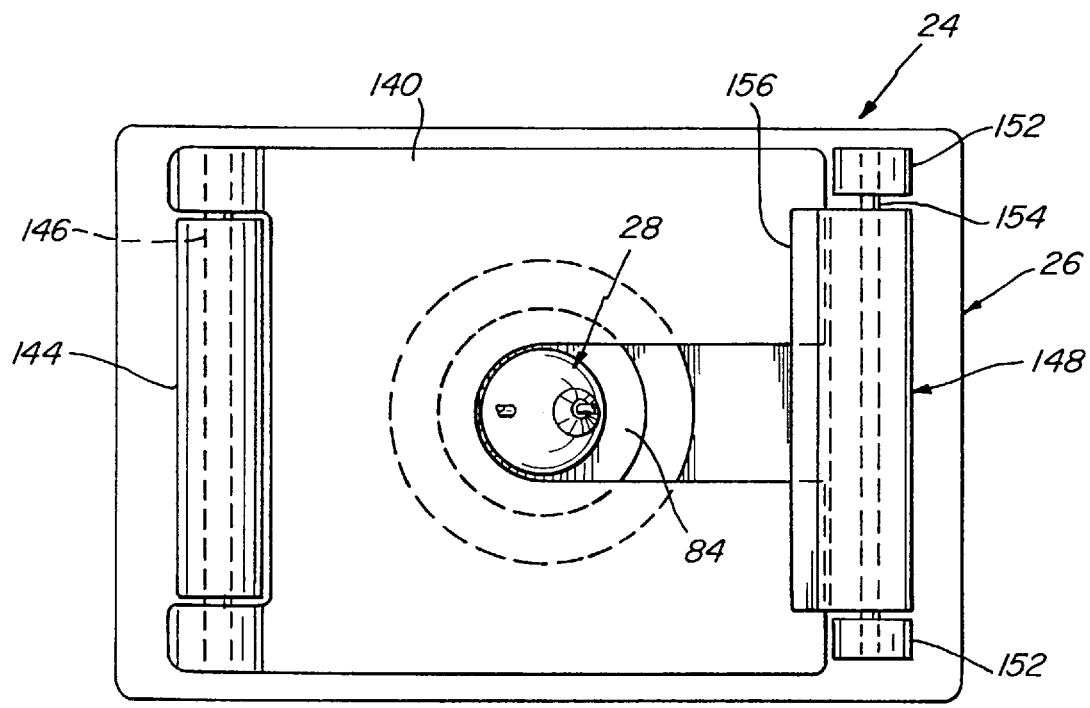

The cartridge 28 is mounted into a compatable socket or opening in the reusable pump housing and is securely retained there by a locking lever 140 and latch 148, side views of which are shown in FIGS. 1 and 2. Other arrangements for releasably engaging the reusable and disposable pump heads may be employed as would be apparent to those of skill in the art. For example, threadable engagement of the reusable and disposable pump housing is envisioned. A radially extending flange or shoulder 84 of the pumping cartridge is engaged by the lever. One end of the locking lever 140 is pivotally connected to the housing by a lever mount 144 and a pin 146. The pin allows the bar to pivot about the hinge mount. A latch 148, which has an inverted L-shape, is pivotally mounted by a pin 154 and a latch mount 152. FIG. 4 shows the latching mechanism from above.

To lock the pump housings together, the locking lever is swung over and against the shoulder of the cartridge. The latch is then tilted to allow an extension 156 to engage the end of the lever. A safety switch (not shown) is provided on the lever to prevent the operation of the pump when the lever is in the unlocked position. When unlocking the cartridge from the pump housing, the latch is pivoted away from the locking bar and the extension 156 is disengaged allowing removal of the cartridge.

Figure 3:
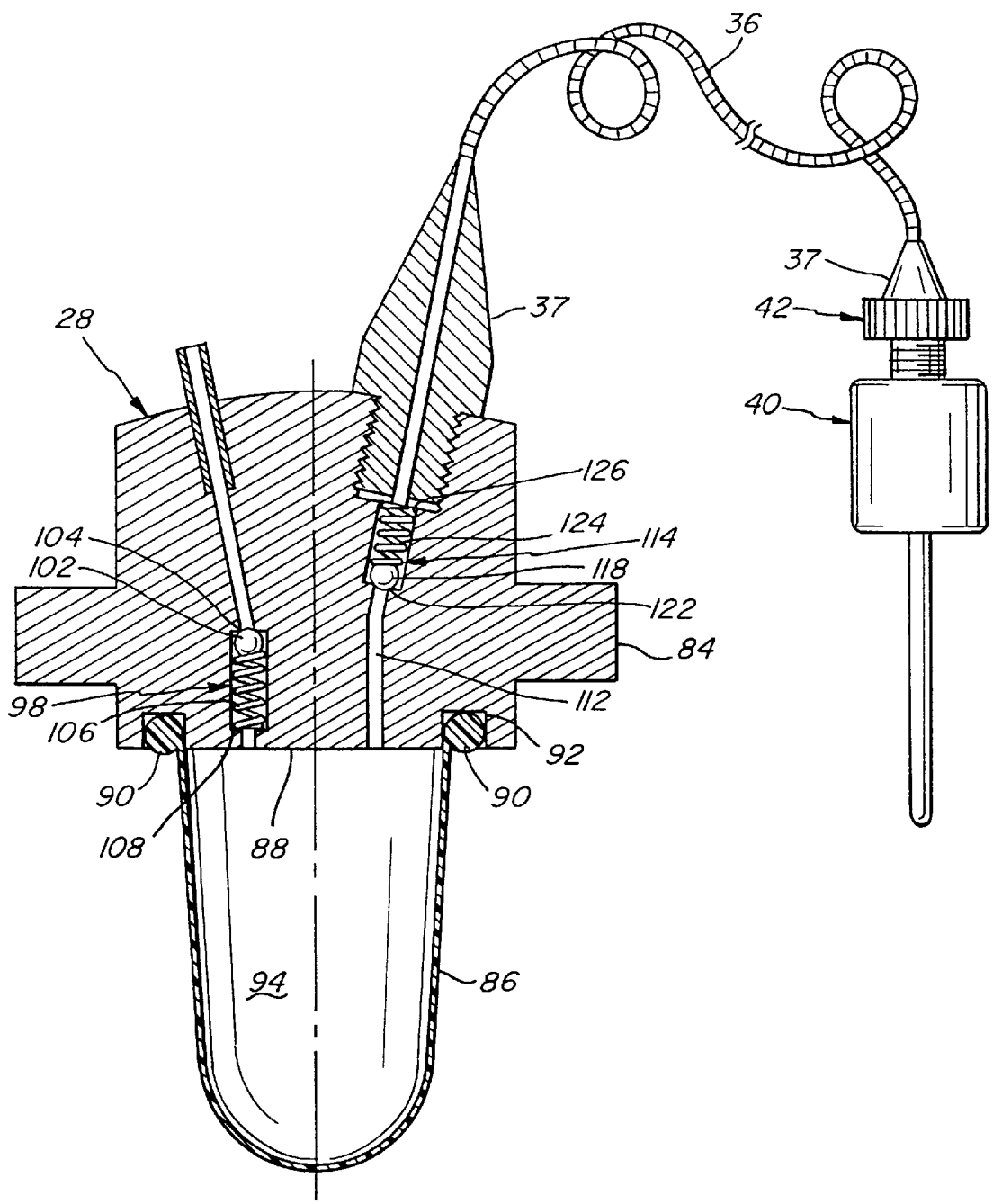
FIG. 3 is a sectional illustration of the disposable diaphragm pump component of the variable high pressure pump; and, FIG. 4 is a top view illustration of the latching mechanism which secures the cartridge to the reusable pump housing.

The disposable pumping cartridge 28 is illustrated in FIG. 3 and includes a flexible, medical grade urethane diaphragm 86 which is mounted on a lower surface 88 of the pumping cartridge. The cartridge may be made of type 304 or 316 stainless or a plastic such as a fiber filled acetal. An annular seal 90, preferably integrally formed with the periphery of the diaphragm and formed of the same urethane material, is seated in an annular channel 92. The seal may be press fit into the channel 92. Alternatively, a "snap fit" may be used whereby a ridge is provided which enables the seal to snap into place. The seal and channel have different cross-sectional shapes; in the illustrated embodiment the seal has a circular cross-section while the channel has a square cross-section. When the cartridge is mounted to the reusable pump housing, the seal is compressed into a shape which conforms with the annular channel. The size and cross sectional geometries for the seal and the channel are such that when the cartridge is latched to the pump housing stress is applied to the O-ring. When the round O-ring cross section deforms into the rectangular cross sectional shape of the annulus, the modulus of elasticity of the seal increases to a value closer to the range of a hard plastic or soft metal, allowing the compressed seal to withstand the elevated pressures contemplated by the pumping system.

A passage extends from an inlet port communicable with a source of saline to a variable sized pumping chamber defined by the deformable diaphragm. A one way valve 98 controls the flow into the chamber and prevents backflow into the sterile fluid source. The check valve illustrated includes a ball 102 that is biased toward a valve seat 104 by one end of a coil spring 106. The other end of the spring rests on an annular lip 108 on the enlarged portion of the housing defining the inlet passage. Other check valves may be employed as would be apparent to those skilled in the art.

A passage 112 extends between an outlet communicable with the high pressure delivery tube and the pumping chamber. A one way valve 114 controls the flow of pumped fluid during the ejection stroke and includes a ball 118 which is biased toward a valve seat 122 by one end of a coil spring 124. The other end of the spring rests on a lip 126 on an enlarged portion defining the outlet passage. Retracting the piston draws the diaphragm away from the disposable housing, reducing the pressure in the pumping chamber. The inlet check valve opens, allowing saline to fill the pumping chamber. Extending the piston increases the pressure in the pumping chamber, opening the outlet check valve and driving the pressurized fluid out of the pump and into the delivery tube.

Preferably, the cartridge is installed in the compatible socket in the reusable pump housing just prior to surgery. The cartridge is mounted on the housing with the diaphragm draping into the mouth of the working fluid chamber. The locking lever is engaged to the latch, compressing the seal and securing the reusable and disposable pump heads together. If air is present in the working fluid chamber, such air should be removed prior to jet cutting. A tube running from a saline bag may be connected to the inlet of the disposable cartridge and the burst resistant, coiled delivery tube may be attached to the outlet of the diaphragm pump.

The assembled pump is inverted on an axis 180, as suggested by arrow 182 (shown in FIGS. 1 and 2) and primed with working fluid. Valve 79 controls the introduction of water while air is allowed to escape through the passage 80 and valve 81. Slowly moving the piston within the working fluid chamber facilitates priming. Valve 81 is closed, after the chamber is filled, while pressure continues to be applied to the passage 78. The primed pump is ready for use.

The pump remains inverted during use to prevent air bubbles from accumulating in the working fluid chamber, allowing the bubbles to float into the annular reservoir when the piston is in the fully retracted position. The piston, preferably, may cycle up to 60 times a second. The pump speed may be selectively controlled by the user via a control dial, a foot or hand switch (not shown), allowing the pressure and cutting strength of the fluid jet to be varied in real.

A representative procedure, in this case a meniscectomy, employing the fluid jet cutting system will now be described. The patient is anesthetized and a tourniquet is applied to the thigh of the leg and set to a pressure of 280 mm Hg. The patient is prepped and draped in a conventional manner. Saline is introduced to the knee either through a superior medial portal using an inflow cannula (three portal technique) or through a scope cannula placed in the lateral portal at the joint line (two portal technique). The saline exists the knee cavity out of medial portion at the joint line. The pathology of the knee is visualized through a scope. After bending the knee, valgus or varus stress is applied to facilitate the approach to tight compartments. Suction may be applied to clear tissue debris and to maintain a clear field of view. The tip of the jet wand may be shaped to facilitate access into the cutting location and to provide a proper cutting orientation of the jet stream. The jet stream is introduced at a low pressure while the cutting site is pinpointed. When the jet and target coincide, the pressure of the stream is increased within the cutting range to resect the tissue. The jet stream also breaks up the resected tissue into smaller fragments. After completing the surgery, the cutting instruments and scope are removed from the portals and the knee is drained and wrapped.

It should be understood that the foregoing description of the invention is intended merely to be illustrative thereof and that other equivalents, embodiments and modifications of the invention may be apparent to those skilled in the art.

What is claimed is:

1. A method of pin-pointing and cutting a target with a fluid jet, comprising the steps of:

providing a fluid jet system including a variable pressure pump, a source of fluid in communication with the pump, a delivery tube in communication with an outlet of the pump and an instrument in communication with the delivery tube having an orifice for creating a fluid jet as the pumped fluid exits therefrom;

pumping fluid at a low pressure through the instrument to create a low pressure jet;

directing the low pressure jet onto a target to pinpoint the target to be cut;

pumping the fluid at a higher pressure while maintaining the jet on the target;

wherein cutting of the target is achieved at the higher pressure, while the jet at the lower pressure is unable to cut the target.

2. The method as recited in claim 1 further comprising the step of utilizing the jet to break up the cut target into smaller fragments.

3. The method as recited in claim 1 wherein the low pressure includes pressures less than 1,000 p.s.i.

4. The method as recited in claim 1 wherein the higher pressures includes pressures greater than 1,000 p.s.i.

5. The method as recited in claim 1 further comprising the step of dispersing a visually observable dye in the fluid before the low pressure jet is directed onto the target.

6. The method as recited in claim 1 wherein the target is supported by the human body.

7. The method as recited in claim 6 wherein the target is tissue.

8. The method as recited in claim 6 wherein the target is bone.

\* \* \* \* \*